United States Patent [19]

Schreinemakers

[11] Patent Number: 4,684,343

[45] Date of Patent: Aug. 4, 1987

[54] IMPRESSION TRAY FOR A DENTATE HUMAN JAW

[76] Inventor: Josephus Schreinemakers, Oranje Nassaulaan 12, NL 6026 BX Maarheeze, Netherlands

[21] Appl. No.: 863,802

[22] Filed: May 9, 1986

Related U.S. Application Data

[63] Continuation of Ser. No. 679,732, Dec. 10, 1984, abandoned.

[30] Foreign Application Priority Data

Dec. 10, 1983 [DE] Fed. Rep. of Germany ....... 3344774

[51] Int. Cl.$^4$ ............................................. A01C 9/00
[52] U.S. Cl. ................................................... 433/214
[58] Field of Search .................................. 433/214, 37

[56] References Cited

U.S. PATENT DOCUMENTS

| 3,619,903 | 11/1971 | Schreinemakers | 433/37 |
| 3,690,004 | 9/1972 | Frush | 433/37 |
| 3,878,610 | 4/1975 | Coscina | 433/37 |
| 4,085,507 | 4/1978 | Lehn et al. | 433/37 |

FOREIGN PATENT DOCUMENTS 1566220 5/1967 Fed. Rep. of Germany ........ 433/37

Primary Examiner—Robert Peshock
Attorney, Agent, or Firm—Karl F. Ross; Herbert Dubno; Andrew Wilford

[57] ABSTRACT

An impression tray for a dentate human jaw having a mobile mucosa and a stationary mucosa with a linear action boundary between the mucosae, the tray having an envelope which in plan follows the U-shape of the dental arch of the jaw and which has a U-shaped trough cross-section near the dental arch, the envelope having a buccal edge and a lingual edge or a palatal edge, the buccal edge and the lingual or palatal edge terminating substantially in the region of the mobile mucosa, the envelope being fillable with an impression material and being pressable onto the jaw. The U-shaped trough cross-section of the envelope extends around the associated dental arch and the stationary mucosa at a distance from them of less than 5 mm, preferably approximately 1 mm. The buccal edge and the lingual edge or palatal edge are pressable onto the mobile mucosa as a sealing strip beyond the action boundary near the mobile mucosa at least with the mobile mucosa mobilized. A narrow gap of, for example, at most 1 mm width can be left in places.

2 Claims, 10 Drawing Figures

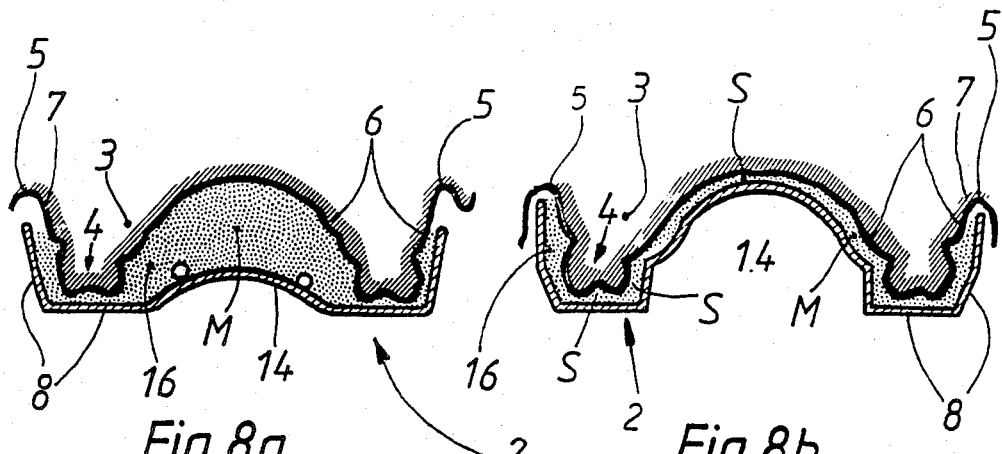
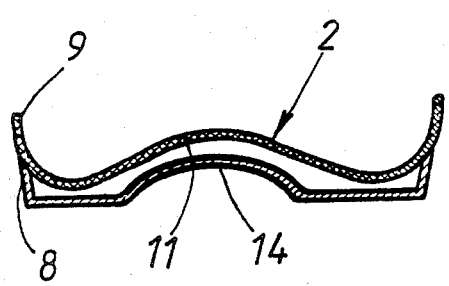
Fig.8a (PRIOR ART)
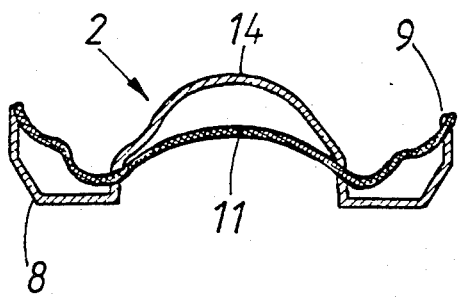
Fig.8b
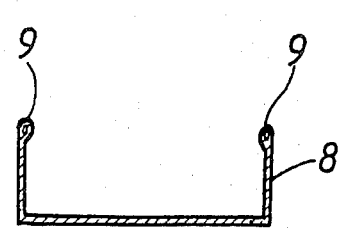
Fig.9a (PRIOR ART)
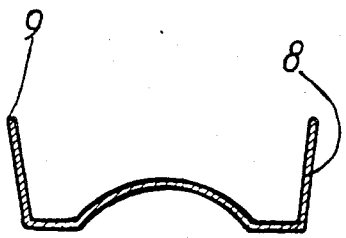
Fig.9b
Fig.10a (PRIOR ART)
Fig.10b

IMPRESSION TRAY FOR A DENTATE HUMAN JAW

This is a continuation of co-pending application Ser. No. 679,732 filed on 10 December 1984, now abandoned.

FIELD OF THE INVENTION

The invention relates to an impression tray for a dentate human jaw having a mobile mucosa and a stationary mucosa and a linear action boundary between the two mucosae, the tray having an envelope which in plan follows the U-shape of the dental arch of the jaw and which has a U-shaped trough cross-section near the dental arch, the envelope having a buccal edge and, in the lower-jaw embodiment, a lingual edge or, in the upper-jaw embodiment, a palatal edge on a palatal vault, the buccal edge and the lingual edge or palatal edge terminating substantially in the region of the mobile mucosa, the envelope being fillable with a high-viscosity impression material and being pressable on the jaw.

BACKGROUND OF THE INVENTION

Impression trays adapted to receive the impression material and to be pressed against the dentate mucosae to take an impression for a dental prosthesis are conventional and standardized in various sizes.

It is the dentist's job so to select the tray shape that corresponds to the shape of the jaw with the dental arch of which an impression is to be taken.

The viscosity of the impression material is, for instance, between $0.5 \times 10^6$ to $1.2 \times 10^6$ millipoise—i.e. the impression material is fairly rigid.

In conventional impression trays of this kind, the U-shaped trough cross-section of the envelope extends around the associated dental arch and the stationary mucosa at a distance from them of more than 5 mm and often as much as 10 mm or more.

Both the labial edge and the lingual or palatal edge terminate at irregular distances from the associated zones of the mucosae and have too much free space between the tray edge and the corresponding mucosa to be able to be of any use as a sealing strip. To this extent, the impression is, as it were, prepared with an open envelope.

When the known trays are used, zones arise in which relatively large volumes of impression material may be relatively passive whereas other parts of the impression are relatively thin. In the case of upper-jaw trays this applies more particularly to the gum region with which a special but flat and less pronounced palatal vault is associated in the known trays. This leads to disadvantages.

Often, the impression is not accurate enough in the whole—i.e., macroscopically speaking. Microscopically, it does not allow for precision modeling of the teeth and all the fine details of the jaw and gum. For instance, it fails to give a clear reproduction of gum pockets, topographical peculiarities of individual teeth, the shape of inlay preparations and other fine detail.

Both the upper-jaw and lower-jaw impressions prepared with known impression trays are insufficiently accurate.

OBJECT OF THE INVENTION

It is the object of the invention to provide an impression tray such that both upper-jaw and lower-jaw impressions can be taken which are completely satisfactory macroscopically and which are precision impressions microscopically.

SUMMARY OF THE INVENTION

According to the invention, therefore, the U-shaped trough cross-section of the envelope extends around the associated dental arch and the stationary mucosa at a distance from them of less than 5 mm, preferably approximately 1 mm, and the buccal edge and the lingual edge or palatal edge are pressable onto the mobile mucosa as a sealing strip beyond the action boundary near the mobile mucosa at least with the mobile mucosa mobilized.

If possible, the tray should be pressed onto the mobile mucosa everywhere. In zones where this cannot be done, a narrow gap of, for instance, 1.5 mm is permissible between the tray edge and the tissue. The result of mobilizing the mucosae is that a relatively uniform tension arises in all parts of the edge between the same and the mucosae. Of course, impression trays according to the invention are made and standardized in various sizes like the known impression trays, the dentist having to select the tray of the correct size.

The starting point for the invention is that if the necessary macroscopic shaping and microscopic accuracy is to be achieved, an impression must be taken, as it were, with a substantially closed shaping or molding space; also, the finished impression must be of substantially equal layer thickness throughout.

Zones where there may be large quantities of impression material must be avoided since the impression material hardly moves in such zones, and so air in the form of bubbles may readily be trapped on the impression surface. Also, the flow intensity is reduced, and so contact with the object to be copied is less, with impairment of accuracy.

The invention is further based on the fact that in the taking of an impression, the impression material must, as it were, be pressurized, so that more intensive contact with the object to be copied is possible. The invention achieves this in that both the buccal edge and the lingual edge or palatal edge are pressable on the mobile mucosa mainly as a sealing strip beyond the action boundary near the mobile mucosa at least with the mobile mucosa mobilized.

Consequently, when the same is mobilized—i.e., if, for instance, the patient is caused to advance his tongue while a lower-jaw impression is being taken or to lower his top lip and cheeks when an upper-jaw impression is being taken—pressure builds up in the molding space between, on the one hand, the patient's teeth and the jaw and, on the other hand, the impression tray according to the invention because the mucosae mobilization referred to tends to close the molding space, and so because of the sealing action of the edges mentioned the impression material cannot readily escape in response to the pressure.

A hydraulic effect is therefore produced and the accuracy of the impression is enhanced. Preferably, in the case of a lower-jaw tray when the same is held horizontally but inverted and viewed from the side, the lingual edge rises rearwardly from a bottom zone in the buccal region to a raised part, then descends in the furthest posterior regions. In the upper-jaw embodiment having a palatal vault and a palatal edge bounding the same, when the tray is held horizontally and viewed from the side, the palatal vault extends from 2 to 8 mm, preferably approximately 5 mm, above the buccal edge. Of course, the edges referred to of an impression tray according to the invention are formed with recesses for the mucosae by way of lateral ligaments and frena.

BRIEF DESCRIPTION OF THE DRAWING

The invention will be described in greater detail hereinafter with reference to the accompanying drawing illustrating merely one embodiment. Throughout the drawing prior art impression trays are shown on the left and, by way of comparison, the impression trays according to the invention are shown on the right. In the drawing:

FIGS. 8a and 8b are each a section along the lines VIIIa—VIIIa and VIIIb—VIIIb of FIGS. 6a and 6b, respectively;

FIGS. 9a and 9b are a rear view of the tray of FIGS. 6a and 6b, respectively; and FIGS. 10a and 10b are sections taken along the lines Xa—Xa and Xb—Xb of FIGS. 6a and 6b, respectively.

SPECIFIC DESCRIPTION

Figures 3A, 3B:
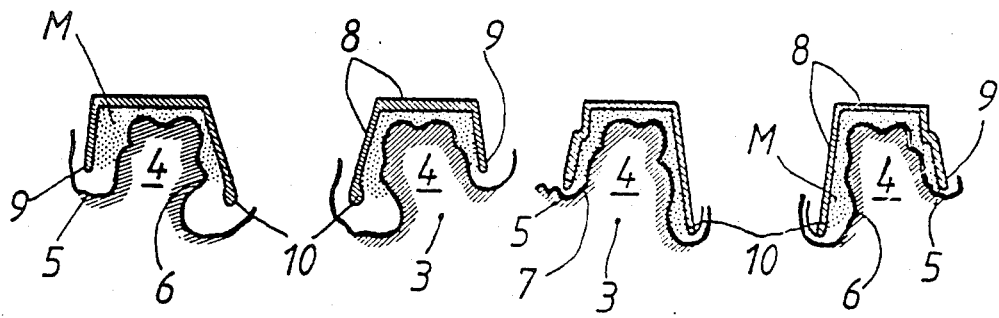
FIGS. 3a and 3b are sections along the lines IIIa—IIIa and IIIb—IIIb in FIGS. 1a and 1b, respectively.

Impression trays 1, 2 shown in the drawings are for use with a dentate human jaw 3. To make the relationships clear, the jaws 3 and the dental arches 4 are shown in FIGS. 3a and 3b and in FIGS. 4a and 4b and in FIGS. 8a and 8b. Each jaw 3 has a mobile mucosa 5 and a stationary mucosa 6 and a linear action boundary 7 between the two mucosae. This is shown in the Figures which have just been mentioned which show the jaw 3.

As can be gathered from the drawings, each tray 1, 2 has an envelope 8 which in plan follows the U-shape of the dental arch 4 of the jaw 3 and which has a U-shaped trough cross-section near the arch 4. The envelope 8 has a buccal edge 9 and a lingual edge 10 or a palatal edge 11. The lingual edge 10 is found on the lower-jaw tray 1 and the palatal edge 11 on the upper-jaw tray 2. The buccal edge 9 and the lingual edge 10 or palatal edge 11 terminate near the mobile mucosa 5. To take an impression, the envelope 8 is filled with a known fairly stiff impression material M and pressed onto the jaw 3.

As can be gathered more particularly from FIGS. 3a and 3b and FIGS. 8a and 8b, the U-shaped trough cross-section of the envelope 8 extends around the associated dental arch 4 and the stationary mucosa 6 at a distance S from them of less than 5 mm, preferably approximately 1 mm. Also, both the buccal edge 9 and the lingual edge 10 or palatal edge 11 can be pressed on to the mobile mucosa 5 as a sealing strip substantially uniformly over their entire extent beyond the action limit 7 near the mobile mucosa 5, at least with the mobile mucosa 5 mobilized. (exceptionally, a gap of, for example, at most 1 mm is permissible over a short distance between an edge and the tissue). This is apparent more particularly from FIGS. 3b and 8b.

Figures 1A, 1B:
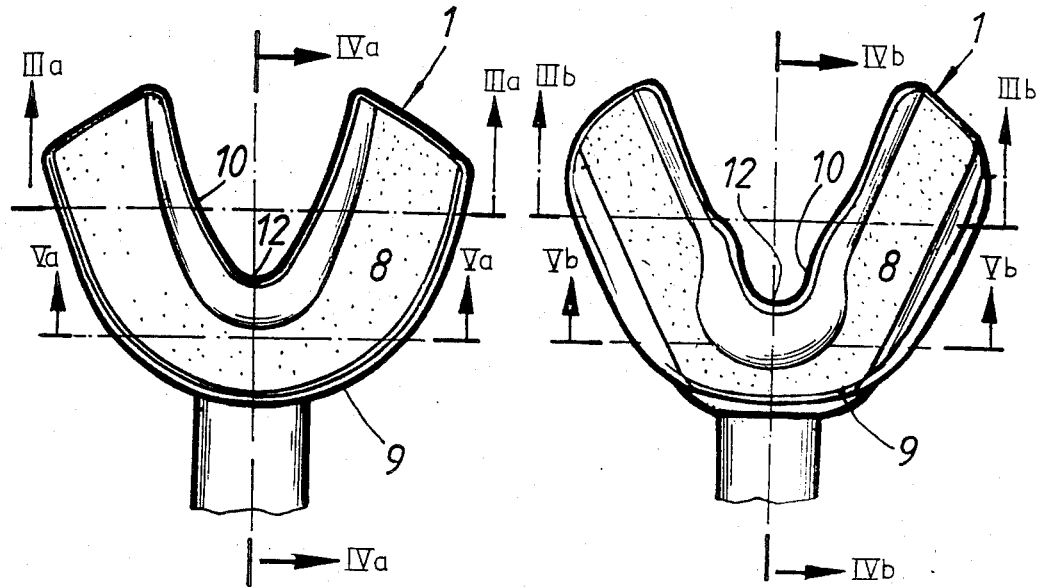
FIGS. 1a and 1b are plan views of a prior art lower-jaw impression tray (FIG. 1a) and a lower jaw impression tray according to the invention (FIG. 1b)
Figure 2A:
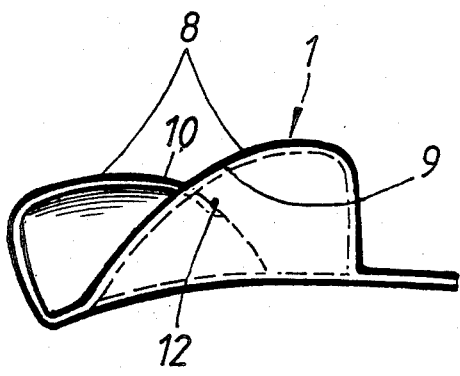
FIGS. 2a and 2b are side views corresponding to FIGS. 1a and 1b, respectively.
Figure 2B:
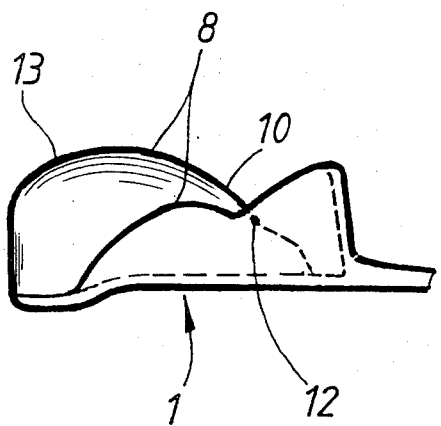
Figures 5A, 5B:
FIGS. 5a and 5b are sections along the lines Va—Va and Vb—Vb of FIGS. 1a and 1b, respectively.
Figures 6A, 6B:
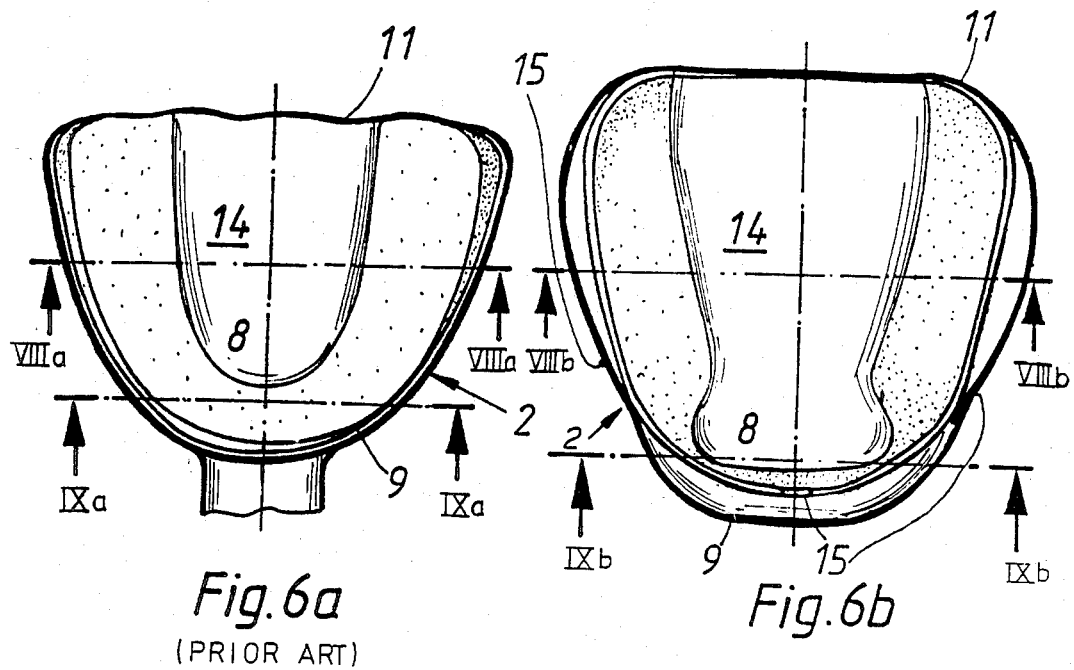
FIGS. 6a and 6b are views corresponding to FIGS. 1a and 1b, respectively, of upper-jaw impression trays.
Figures 7A, 7B:
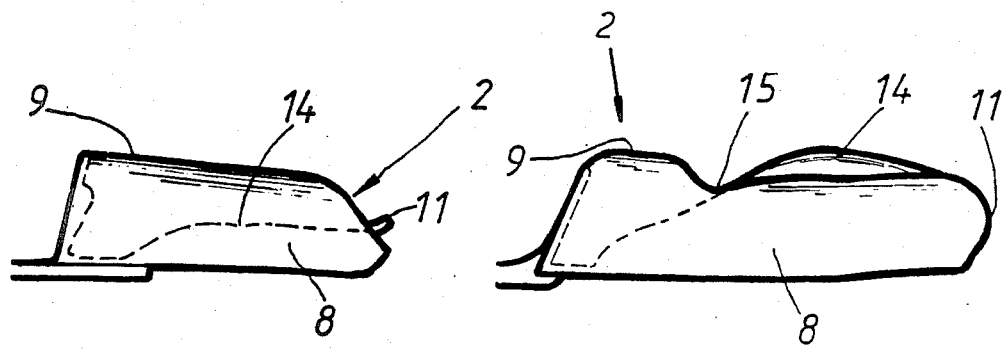
FIGS. 7a and 7b are side views corresponding to FIGS. 6a and 6b, respectively.

FIGS. 1b and 5b show the lower-jaw impression tray embodiment 1. As is apparent, when the tray 1 is held horizontally and inverted and viewed from the side (FIG. 2b), the lingual edge 10 rises from a bottom part 12 in the buccal region to a raised part 13 further back in the mouth.

FIGS. 6b to 10b show the upper-tray embodiment 2 with a palatal vault 14 and a palatal edge 11 bounding the same. As is apparent, when the tray 2 is held horizontally and viewed from the side, as shown in FIG. 7b, the vault 14 extends from 2 to 8 mm, at most some 5 mm in the embodiment, above the buccal edge 9. The various edges 9, 10, 11 are of course formed with recesses 15 for the ligaments which in the corresponding zones connect muscles of facial expression to the bone.

Figures 4A, 4B:
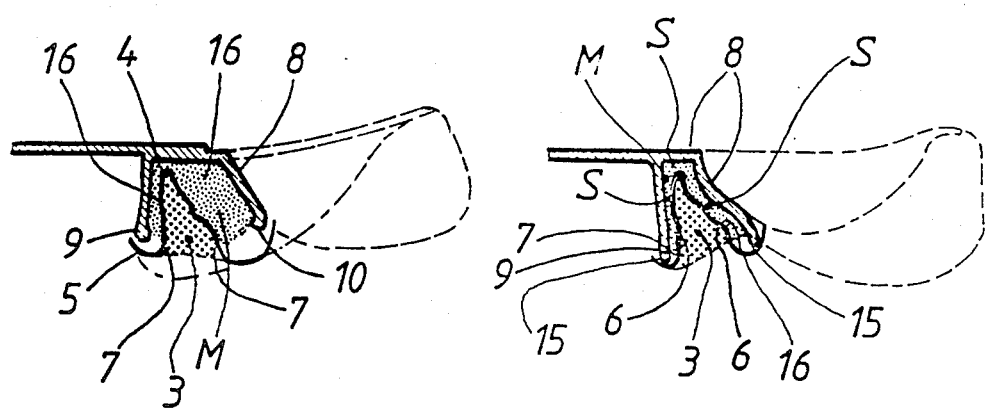
FIGS. 4a and 4b are sections along lines IVa—IVa and IVb—IVb of FIGS. 1a and 1b, respectively.

FIGS. 3b, 8b and even FIG. 4b show clearly that a closed molding space 16 arises when working with an impression tray 1 or 2 according to the invention and the pressure necessary for an accurate impression can be produced in the space 16 either previously or by mobilizing those zones of the mobile mucosa 5 which are adjacent the sealing strip. There are no large voids in which impression material M might experience less movement. On the other hand, when working with the prior-art impression trays 1, 2 voids of this kind arise and the molding space 16 is completely open, as can be gathered more particularly from FIGS. 3a, 4a and 8a.

I claim:

1. A method of using a U-shaped, U-section, and imperforate tray having a buccal edge and an opposite lingual/palatal edge to take an impression of a human patient's jaw having a hard U-shaped dental arch, a mobile mucosa and a stationary mucosa to each side thereof, at least one tooth, and a linear action boundary between the two mucosae, the method comprising the steps of:

selecting from a set of anatomically differently dimensioned such trays the tray capable of fitting over the dental arch of the current patient with the buccal edge outside the arch and the lingual/palatal edge within the arch, with the tray generally uniformly spaced at most 5 mm from the arch, and with the buccal and lingual/palatal edges engaging the mobile mucosa generally beyond the linear action boundary;

filling the selected tray with a high-viscosity impression material;

pressing the filled and selected tray over said current patient's dental arch to press the buccal and lingual/palatal edges into tight engagement against the mobile mucosa past the linear action boundary with the tray generally uniformly spaced at most 5 mm from the arch to form between the tray and the dental arch a substantially closed and generally constant-section chamber hydraulically confining the impression material; and compressing the confined material in the chamber against the dental arch by pressing the tray toward the arch while mobilizing the mobile mucosa to hydraulically press the confined material into form-fit engagement with the stationary mucosa and without substantial leakage of the impression material from the chamber.

2. The impression-taking method defined in claim 1 wherein the spacing in the selecting and pressing steps is about 1 mm.

* * * * *